(12) United States Patent
Gozani et al.

(10) Patent No.: US 11,191,443 B2
(45) Date of Patent: Dec. 7, 2021

(54) DETECTING CUTANEOUS ELECTRODE PEELING USING ELECTRODE-SKIN IMPEDANCE

(71) Applicant: NeuroMetrix, Inc., Waltham, MA (US)

(72) Inventors: Shai Gozani, Newton, MA (US); Xuan Kong, Acton, MA (US); Andres Aguirre, Belmont, MA (US); Tom Ferree, Waltham, MA (US)

(73) Assignee: NeuroMetrix, Inc., Woburn, MA (US)

( * ) Notice: Subject to any disclaimer, the term of this patent is extended or adjusted under 35 U.S.C. 154(b) by 212 days.

(21) Appl. No.: 16/231,673

(22) Filed: Dec. 24, 2018

(65) Prior Publication Data

US 2019/0269909 A1 Sep. 5, 2019

Related U.S. Application Data

(63) Continuation of application No. 15/332,367, filed on Oct. 24, 2016, now Pat. No. 10,159,835, which is a (Continued)

(51) Int. Cl.
*A61B 5/0531* (2021.01)
*A61N 1/36* (2006.01)
(Continued)

(52) U.S. Cl.
CPC ............ *A61B 5/0531* (2013.01); *A61B 5/486* (2013.01); *A61B 5/6828* (2013.01);
(Continued)

(58) Field of Classification Search
CPC ..... A61B 5/0531; A61B 5/6828; A61B 5/486; A61N 1/3603
(Continued)

(56) References Cited

U.S. PATENT DOCUMENTS

| 1,741,962 A | 12/1929 | Theodoropulos |
| 4,290,431 A | 9/1981 | Herbert et al. |

(Continued)

FOREIGN PATENT DOCUMENTS

| CN | 1665563 | 9/2005 |
| CN | 1919139 | 2/2007 |

(Continued)

OTHER PUBLICATIONS

Amazon, "Quell 2.0 Wearable Pain Relief Technology", Sep. 15, 2018.http://www.amazon.com/Quell-Wearable-Pain-Relief-Technology/dp/B07DHW2MJJ/ref=cm_cr_arp_d_product_top?ie=UTF8. Shown on p. 1. (Year: 2018).

(Continued)

*Primary Examiner* — Amanda K Hulbert
*Assistant Examiner* — Philip C Edwards
(74) *Attorney, Agent, or Firm* — Pandiscio & Pandiscio

(57) ABSTRACT

Apparatus for transcutaneous electrical nerve stimulation in a user, the apparatus comprising:
stimulation means for electrically stimulating at least one nerve;
an electrode array connectable to said stimulation means, said electrode array comprising a plurality of electrodes for electrical stimulation of the at least one nerve, said electrodes having a pre-formed geometry and known electrode-skin contact area size when in complete contact with the user's skin;
monitoring means electrically connected to said stimulation means for monitoring the impedance of the electrical stimulation through said electrode array; and
analysis means for analyzing said impedance to estimate a change in the electrode-skin contact area.

24 Claims, 9 Drawing Sheets

Related U.S. Application Data continuation of application No. 14/230,648, filed on Mar. 31, 2014, now Pat. No. 9,474,898.

(60) Provisional application No. 61/806,481, filed on Mar. 29, 2013.

(51) Int. Cl.
*A61N 1/04* (2006.01)
*A61B 5/00* (2006.01)

(52) U.S. Cl.
CPC ......... *A61N 1/0456* (2013.01); *A61N 1/0492* (2013.01); *A61N 1/3603* (2017.08); *A61N 1/36021* (2013.01); *A61B 2560/0276* (2013.01)

(58) Field of Classification Search
USPC .......................................................... 607/46
See application file for complete search history.

(56) References Cited

U.S. PATENT DOCUMENTS

| | | |
|---|---|---|
| D263,869 S | 4/1982 | Sumiyasu |
| 4,503,863 A | 3/1985 | Katims |
| 4,605,010 A | 8/1986 | McEwen |
| 4,738,250 A | 4/1988 | Fulkerson et al. |
| 4,989,605 A | 2/1991 | Rossen |
| 5,048,523 A | 9/1991 | Yamasawa et al. |
| 5,063,929 A | 11/1991 | Bartelt et al. |
| 5,121,747 A | 6/1992 | Andrews |
| 5,169,384 A | 12/1992 | Bosniak et al. |
| D342,571 S | 12/1993 | Givens, Sr. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,948,000 A | 9/1999 | Larsen et al. |
| 6,099,488 A | 8/2000 | Hung |
| 6,161,044 A | 12/2000 | Silverstone |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,611,789 B1 | 8/2003 | Darley |
| 6,662,051 B1 | 12/2003 | Eraker et al. |
| D541,042 S | 4/2007 | Andre et al. |
| D566,383 S | 4/2008 | Hamis et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,829 S | 10/2010 | Arbesman et al. |
| D629,115 S | 12/2010 | Robertson |
| 7,887,493 B2 | 2/2011 | Stahmann et al. |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| 8,284,070 B2 | 10/2012 | Chaudhari et al. |
| D680,735 S | 4/2013 | Itabashi et al. |
| 8,421,642 B1 | 4/2013 | McIntosh et al. |
| D688,707 S | 8/2013 | Vincent et al. |
| D705,428 S | 5/2014 | Cheney et al. |
| D712,045 S | 8/2014 | Thornton |
| 8,825,175 B2 | 9/2014 | King |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| 9,168,375 B2 | 10/2015 | Rahimi et al. |
| D744,661 S | 12/2015 | Rizzi |
| D750,263 S | 2/2016 | Shigeno et al. |
| D750,798 S | 3/2016 | Yosef et al. |
| 9,282,287 B1 | 3/2016 | Marsh |
| 9,282,897 B2 | 3/2016 | Ross, Jr. et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| 9,700,724 B2 | 7/2017 | Liu et al. |
| D794,331 S | 8/2017 | Grote |
| 9,731,126 B2 | 8/2017 | Ferree et al. |
| D801,542 S | 10/2017 | Anderson |
| D802,780 S | 11/2017 | Hsu |
| 9,827,420 B2 | 11/2017 | Ferree et al. |
| D806,669 S | 1/2018 | Kangasmaa et al. |
| D810,843 S | 2/2018 | Karvandi |
| D811,729 S | 3/2018 | Bysshe |
| D813,405 S | 3/2018 | Ho |
| D813,407 S | 3/2018 | Chen |
| D813,408 S | 3/2018 | Chen |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| D837,394 S | 1/2019 | Cryan et al. |
| 10,279,179 B2 | 5/2019 | Gozani et al. |
| 10,335,595 B2 | 7/2019 | Ferree et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0122483 A1 | 6/2004 | Nathan et al. |
| 2005/0059903 A1 | 3/2005 | Izumi |
| 2005/0080463 A1 | 4/2005 | Stahmann et al. |
| 2005/0234525 A1 | 10/2005 | Phillips |
| 2005/0283204 A1 | 12/2005 | Buhlmann et al. |
| 2006/0052788 A1 | 3/2006 | Thelen et al. |
| 2006/0085047 A1 | 4/2006 | Unsworth et al. |
| 2006/0085049 A1 | 4/2006 | Cory et al. |
| 2006/0089683 A1 | 4/2006 | Hagglof et al. |

(56) References Cited

U.S. PATENT DOCUMENTS

| | | |
|---|---|---|
| 2006/0095088 A1 | 5/2006 | De Ridder |
| 2006/0173507 A1 | 8/2006 | Mrva et al. |
| 2006/0190057 A1 | 8/2006 | Reese |
| 2006/0251334 A1 | 11/2006 | Oba et al. |
| 2007/0060922 A1 | 3/2007 | Dreyfuss |
| 2007/0203435 A1 | 8/2007 | Novak |
| 2007/0203547 A1 | 8/2007 | Costello et al. |
| 2007/0276449 A1 | 11/2007 | Gunter et al. |
| 2008/0009772 A1 | 1/2008 | Tyler et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0172102 A1 | 7/2008 | Shalev |
| 2008/0312709 A1 | 12/2008 | Volpe et al. |
| 2009/0030476 A1 | 1/2009 | Hargrove |
| 2009/0076364 A1 | 3/2009 | Libbus et al. |
| 2009/0082829 A1 | 3/2009 | Panken et al. |
| 2009/0112214 A1 | 4/2009 | Philippon et al. |
| 2009/0131993 A1 | 5/2009 | Rousso et al. |
| 2009/0203972 A1 | 8/2009 | Heneghan et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0010585 A1 | 1/2010 | Davis et al. |
| 2010/0042180 A1 | 2/2010 | Mueller et al. |
| 2010/0057149 A1 | 3/2010 | Fahey |
| 2010/0087903 A1* | 4/2010 | Van Herk ............... A61B 5/063 607/115 |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217985 A1 | 8/2010 | Fahey |
| 2010/0241464 A1 | 9/2010 | Amigo et al. |
| 2011/0066209 A1 | 3/2011 | Bodlaender et al. |
| 2011/0166622 A1* | 7/2011 | Crosson ............. A61N 1/36021 607/46 |
| 2011/0190594 A1 | 8/2011 | Heit et al. |
| 2011/0224665 A1 | 9/2011 | Crosby et al. |
| 2011/0245711 A1* | 10/2011 | Katra .................. A61B 5/1072 600/547 |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2012/0123227 A1 | 5/2012 | Sun et al. |
| 2012/0130449 A1 | 5/2012 | Carlyon et al. |
| 2012/0303077 A1 | 11/2012 | De Vincentiis |
| 2012/0319816 A1 | 12/2012 | Al-Ali |
| 2013/0096641 A1 | 4/2013 | Strother et al. |
| 2013/0116514 A1 | 5/2013 | Kroner et al. |
| 2013/0158627 A1 | 6/2013 | Gozani et al. |
| 2013/0217998 A1 | 8/2013 | Mahfouz et al. |
| 2014/0039450 A1 | 2/2014 | Green et al. |
| 2014/0057232 A1 | 2/2014 | Wetmore et al. |
| 2014/0081353 A1 | 3/2014 | Cook et al. |
| 2014/0088192 A1 | 3/2014 | Heller et al. |
| 2014/0107729 A1 | 4/2014 | Sumners et al. |
| 2014/0163444 A1 | 6/2014 | Ingvarsson et al. |
| 2014/0245791 A1 | 9/2014 | Proud et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336730 A1 | 11/2014 | Simon et al. |
| 2014/0371547 A1 | 12/2014 | Gartenberg et al. |
| 2014/0371814 A1 | 12/2014 | Spizzirri et al. |
| 2014/0379045 A1 | 12/2014 | Rahimi et al. |
| 2015/0045853 A1 | 2/2015 | Alataris et al. |
| 2015/0157242 A1 | 6/2015 | Sabesan |
| 2015/0174402 A1 | 6/2015 | Thomas et al. |
| 2015/0272511 A1 | 10/2015 | Najafi et al. |
| 2015/0306387 A1 | 10/2015 | Kong et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2015/0335877 A1 | 11/2015 | Jeffery et al. |
| 2016/0007931 A1 | 1/2016 | Rubin et al. |
| 2016/0113551 A1 | 4/2016 | Annegarn et al. |
| 2016/0144174 A1 | 5/2016 | Ferree et al. |
| 2016/0151628 A1 | 6/2016 | Simon et al. |
| 2016/0189371 A1 | 6/2016 | Krishna Rao et al. |
| 2016/0242646 A1 | 8/2016 | Obma |
| 2016/0367823 A1 | 12/2016 | Cowan et al. |
| 2017/0056650 A1 | 3/2017 | Cohen et al. |
| 2017/0209693 A1 | 7/2017 | An et al. |
| 2018/0028808 A1 | 2/2018 | Ferree et al. |
| 2018/0132757 A1 | 5/2018 | Kong et al. |
| 2018/0177996 A1 | 6/2018 | Gozani et al. |
| 2019/0134393 A1 | 5/2019 | Wong et al. |

FOREIGN PATENT DOCUMENTS

| | | |
|---|---|---|
| CN | 1926496 | 3/2007 |
| CN | 101557788 | 10/2009 |
| CN | 101626804 | 1/2010 |
| CN | 102202131 | 9/2011 |
| CN | 102355847 | 2/2012 |
| CN | 102740919 | 10/2012 |
| DE | 102010052710 | 5/2012 |
| EP | 0971653 | 1/2000 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2015/123373 | 8/2015 |

OTHER PUBLICATIONS

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Ancoli-Israel, S. et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

(56) References Cited

OTHER PUBLICATIONS

Bonnet, M. et al., Recording and Scoring Leg Movements, Sleep, 1993, vol. 16, No. 8, p. 748-759.
Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.
Chandran P et al., Development of opioid tolerance with repeated transcutaneous electrical nerve stimulation administration, Pain, 2003, vol. 102: 195-201.
Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.
Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.
Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.
Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.
Claydon LS et al., Dose-specific effects of transcutaneous electrical nerve stimulation on experimental pain, Clinical Journal of Pain, 2011, vol. 27(7): 635-647.
Cole, R.J et al., Automatic Sleep/Wake Identification From Wrist Activity, Sleep, 1992, 15(5), p. 461-469.
Cruccu G. et al., EFNS guidelines on neurostimulation therapy for neuropathic pain, European Journal of Neurology, 2007, vol. 14: 952-970.
Davies HTO et al., Diminishing returns or appropriate treatment strategy?—an analysis of short-term outcomes after pain clinic treatment, Pain, 1997, vol. 70: 203-208.
Desantana JM et al., Effectiveness of transcutaneous electrical nerve stimulation for treatment of hyperalgesia and pain, Curr Rheumatol Rep. 2008, vol. 10(6): 492-499.
Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.
Fary RE et al., Monophasic electrical stimulation produces high rates of adverse skin reactions in healthy subjects, Physiotherapy Theory and Practice, 2011, vol. 27(3): 246-251.
Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6):639-647.
Fishbain, David A. et al., Transcutaneous Electrical Nerve Stimulation (TENS) Treatment Outcome in Long-Term Users, The Clinical Journal of Pain, Sep. 1996; 12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Hausdorff, J.M. et al., Gait Variability and Fall Risk in Community-Living Older Adults: A 1-Year Prospective Study, Arch Phys Med Rehabil, Aug. 2001, vol. 82, pp. 1050-1056.
Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and TENS-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, MI et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels and Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement. J. Comp. Physiol. Psychol. Oct. 1959; 52:629-634.
Lykken, D.T., Square-Wave Analysis of Skin Impedance. Psychophysiology. Sep. 1970; 7(2):262-275.
MacFarlane, T. et al., Whether the weather influences pain? Results from EpiFunD study in North West England, Rheumatology, 2010, vol. 49, pp. 1513-1520.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Nightingale, S., The neuropathic pain market, Nature Reviews, 2012, vol. 11, p. 101-102.
Okamoto-Mizuno. K et al., Effects of thermal environment on sleep and circadian rhythm, Journal of Physiological Anthropology, 2012, vol. 31, No. 14, pp. 1-9.
Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.
Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.

(56) References Cited

OTHER PUBLICATIONS

Pantaleao MA et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.
Sano, A et al., Quantitative analysis of wrist electrodermal activity during sleep, International Journal of Psychophysiology, 2014, vol. 94, pp. 382-389.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Sheridan et al., Some Factors Influencing the Threshold of the Electrocutaneous Stimulus, Perceptual and Motor Skills, 1966, vol. 22, pp. 647-654.
Susi et al., Motion Mode Recognition and Step Detection Algorithms for Mobile Phone Users, Sensors, Jan. 24, 2013, vol. 13, pp. 1539-1562.
Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.
Tryon, W. W., Issues of Validity in Actigraphic Sleep Assessment, Sleep, 2004, 27(1), p. 158-165.
Tsai, Y. et al., Impact of Subjective Sleep Quality on Glycemic Control in Type 2 Diabetes Mellitus, Family Practice, 2012, vol. 29, p. 30-35.
Van Boxtel, A., Skin resistance during square-wave electrical pulses of 1 to 10 mA. Med. Biol. Eng. Comput. Nov. 1977; 15(6):679-687.
Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.
Waeber, R. et al., Biosection Search with Noisy Responses, SIAM J. Control Optim., 2013, vol. 51, No. 3, pp. 2261-2279.
Webster, J. B. et al., An Activity-Based Sleep Monitor System for Ambulatory Use, Sleep, 1982, 5(4), p. 389-399.
Zelman, D. C. et al., Sleep Impairment in Patients With Painful Diabetic Peripheral Neuropathy, The Clinical Journal of Pain, 2006, 22(8), p. 681-685.
Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

\* cited by examiner

DETECTING CUTANEOUS ELECTRODE PEELING USING ELECTRODE-SKIN IMPEDANCE

REFERENCE TO PENDING PRIOR PATENT APPLICATIONS

This patent application is a continuation of prior U.S. patent application Ser. No. 15/332,367, filed Oct. 24, 2016 by NeuroMetrix, Inc. and Shai Gozani et al. for DETECTING CUTANEOUS ELECTRODE PEELING USING ELECTRODE-SKIN IMPEDANCE, which patent application is a continuation of prior U.S. patent application Ser. No. 14/230,648, filed Mar. 31, 2014 by NeuroMetrix, Inc. and Shai Gozani et al. for DETECTING CUTANEOUS ELECTRODE PEELING USING ELECTRODE-SKIN IMPEDANCE, which claims benefit of prior U.S. Provisional Patent Application Ser. No. 61/806,481, filed Mar. 29, 2013 by Shai Gozani for DETECTING ELECTRODE PEELING BY RELATIVE CHANGES IN SKIN-ELECTRODE IMPEDANCE.

The three (3) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes so as to provide symptomatic relief of pain, and more particularly to detecting "electrode peeling" where the electrodes of the TENS device unintentionally separate from the skin of the user during use.

BACKGROUND OF THE INVENTION

Transcutaneous Electrical Nerve Stimulation (TENS) devices apply electrical currents to a particular area of the human body in order to suppress pain. The most common form of TENS is called conventional TENS. In conventional TENS, electrodes are placed on the skin within, adjacent to, or proximal to, the area of pain. Electrical stimulation is then delivered to the user through the electrodes, with the electrical stimulation being in the form of low intensity (typically less than 100 mA), short duration (typically 50-400 μsec) pulses at frequencies typically between about 10 and 200 Hz.

TENS electrodes typically utilize hydrogels to create a stable low-impedance electrode-skin interface to facilitate the delivery of electrical current to the user so as to stimulate peripheral sensory nerves. A minimum electrode-skin contact area must be maintained in order to ensure that the stimulation current and power densities (power intensity per unit contact area) remain below safe thresholds so as to avoid skin irritation and, in the extreme, thermal burns.

A significant safety concern for traditional TENS use is the potential for "electrode peeling" (i.e., where the electrodes of the TENS device unintentionally separate from the skin of the user) that results in an increased current and power density due to decreased electrode-skin contact area. Increased current and power density could lead to painful stimulation and, in the extreme, thermal burns. The U.S. Food and Drug Administration (FDA) has published draft guidelines on TENS devices that require a warning against the use of such devices during sleep due to the risk of unintended electrode peeling [Food and Drug Administration, *Draft Guidance for Industry and Staff: Class II Special Controls Guidance Document: Transcutaneous Electrical Nerve Stimulator for Pain Relief*, Apr. 5, 2010].

Poor sleep quality is one of the major causes of morbidity in patients suffering from chronic pain [Fishbain D A, Hall J, Meyers A L, Gonzales J, Mallinckrodt C. Does pain mediate the pain interference with sleep problem in chronic pain? Findings from studies for management of diabetic peripheral neuropathic pain with duloxetine. *J Pain Symptom Manage*. December 2008; 36(6):639-647]. It is, therefore, desirable that patients have the option of receiving TENS therapy during sleep. In fact, several studies have shown that TENS therapy can improve sleep quality (see, for example, Barbarisi M, Pace M C, Passavanti M B, et al. Pregabalin and transcutaneous electrical nerve stimulation for postherpetic neuralgia treatment. *Clin J Pain*. September 2010; 26(7):567-572). For these reasons, it would be advantageous to provide automated means to measure electrode-skin contact area in real-time so that TENS devices can be used during sleep for pain relief while safeguarding users from unintended electrode peeling. In particular, when a substantial reduction in electrode-skin area is detected, TENS stimulation should be halted or reduced in order to prevent excessive current or power density over the remaining electrode-skin contact area, thereby preventing painful stimulation and, in the extreme, thermal burns.

SUMMARY OF THE INVENTION

The present invention comprises the provision and use of a novel TENS device which consists of a stimulator designed to be placed on a user's upper calf and a pre-configured electrode array designed to provide circumferential stimulation in the area of the upper calf. A key feature of the present invention is that the TENS device is adapted to measure electrode-skin impedance continuously for monitoring the electrode-skin contact area. The known geometry of the pre-configured electrode array establishes the initial electrode-skin contact area and the analysis of subsequent electrode-skin impedance changes allows prediction of electrode-skin contact area (i.e., to detect electrode peeling). When the electrode-skin impedance reaches a critical value corresponding to a reduced contact area (i.e., as a result of unintended electrode peeling) that may lead to excessive stimulation current or power density, the TENS device automatically terminates or reduces TENS stimulation in order to avoid the risk of painful stimulation and, in the extreme, thermal burns.

In one preferred form of the present invention, there is provided apparatus for transcutaneous electrical nerve stimulation in a user, the apparatus comprising:

stimulation means for electrically stimulating at least one nerve;

an electrode array connectable to said stimulation means, said electrode array comprising a plurality of electrodes for electrical stimulation of the at least one nerve, said electrodes having a pre-formed geometry and known electrode-skin contact area size when in complete contact with the user's skin;

monitoring means electrically connected to said stimulation means for monitoring the impedance of the electrical stimulation through said electrode array; and analysis means for analyzing said impedance to estimate a change in the electrode-skin contact area.

In another preferred form of the present invention, there is provided a method for monitoring electrode-skin contact area while delivering transcutaneous electrical nerve stimulation to at least one nerve of a user through an electrode array comprising a plurality of electrodes, wherein each electrode has a known geometry and size, the method comprising the steps of:

applying the electrode array to the surface of the user's skin to allow a complete contact between the plurality of electrodes and the skin;

electrically stimulating said at least one nerve of the user with an electrical stimulator connected to the electrode array;

monitoring the impedance of the electrode-skin interface; and analyzing the monitored impedance to estimate electrode-skin contact area size.

In another preferred form of the present invention, there is provided apparatus for transcutaneous electrical nerve stimulation in a user, said apparatus comprising:

an electrode array comprising a plurality of electrodes, said plurality of electrodes having a pre-formed geometry and known electrode-skin contact area when said plurality of electrodes are in complete contact with the skin of a user;

stimulation means connectable to said electrode array for providing electrical stimulation to the skin of the user so as to stimulate at least one nerve of the user;

monitoring means electrically connectable to said electrode array for monitoring the electrode-skin impedance value; and control means for controlling the electrical stimulation provided to the skin of the user when the monitoring means determines that the electrode-skin impedance value has changed by a predetermined value.

In another preferred form of the present invention, there is provided a method for applying transcutaneous electrical nerve stimulation to a user, said method comprising:

applying a stimulation current to a user through an anode having an electrode-skin interface and a cathode having an electrode-skin interface;

measuring (i) the stimulation current through, and (ii) the voltage difference between, the anode and the cathode so as to determine electrode-skin impedance; and modifying the stimulation current when the electrode-skin impedance changes in a predetermined manner.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
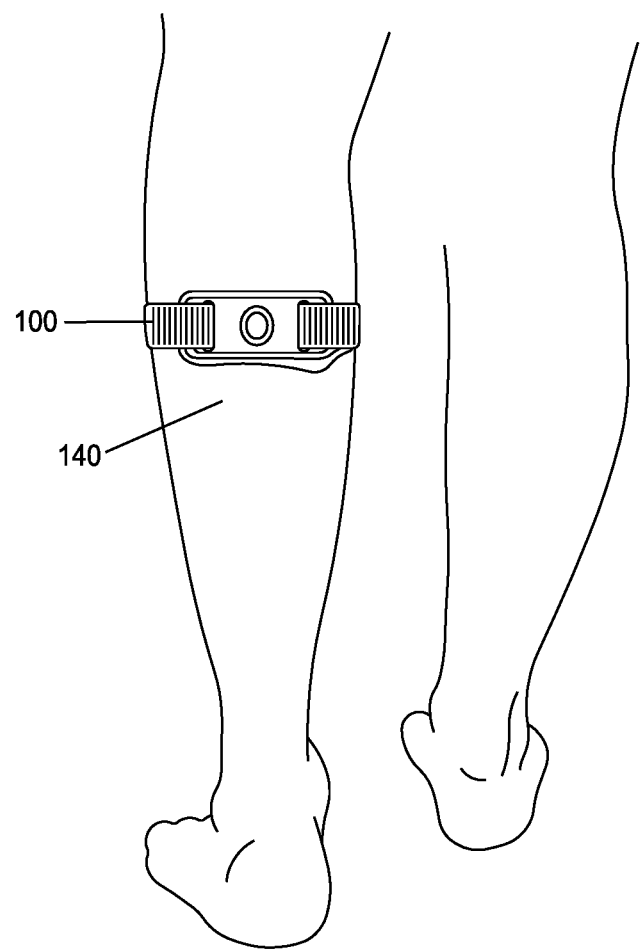
FIG. 1 is a schematic view showing a novel TENS device formed in accordance with the present invention, with the novel TENS device being mounted to the upper calf of a user.
Figure 2:
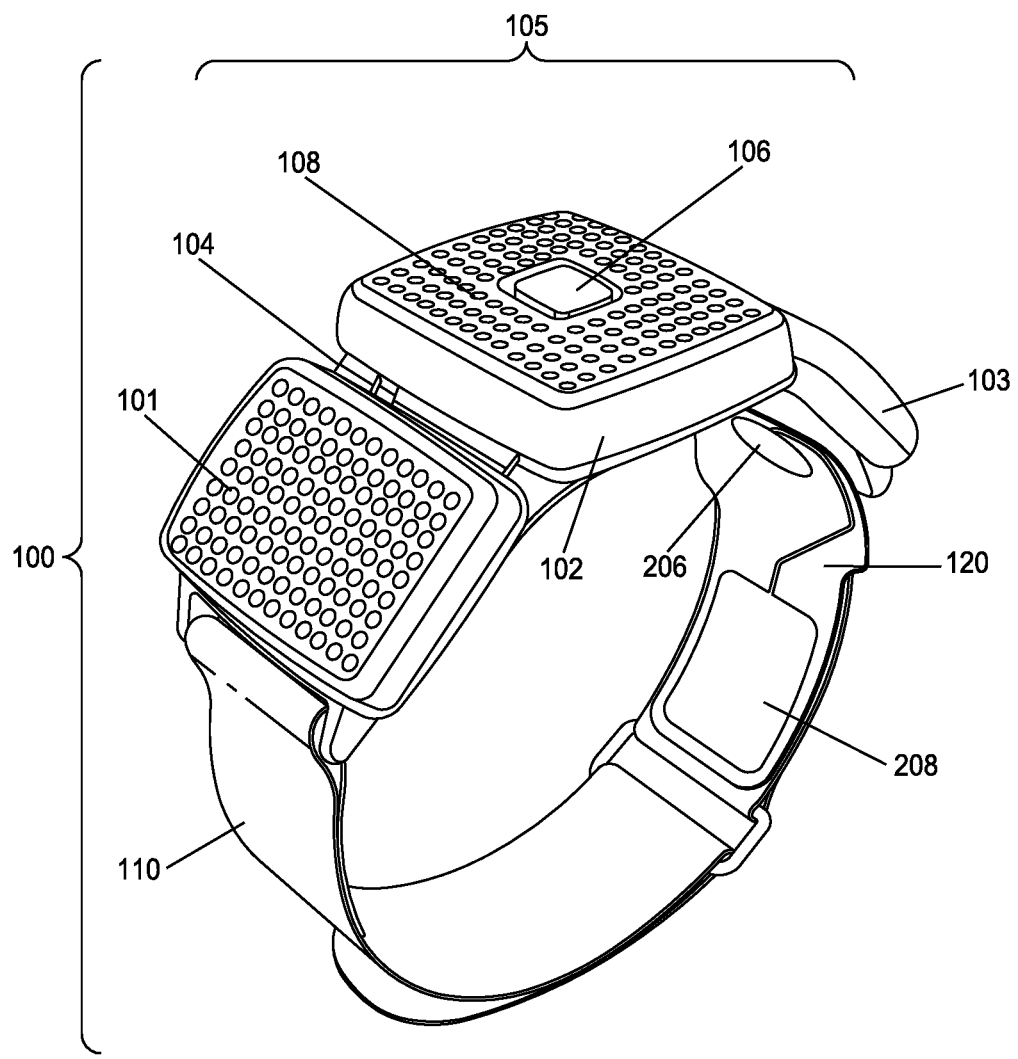
FIG. 2 is a schematic view showing the novel TENS device of FIG. 1 in greater detail.

FIG. 1 illustrates a novel TENS device 100 formed in accordance with the present invention, with the novel TENS device being shown worn on a user's upper calf 140. A user may wear TENS device 100 on one or both legs. TENS device 100 is shown in greater detail in FIG. 2 and preferably comprises three components: a stimulator 105, a strap 110, and an electrode array 120. Stimulator 105 preferably comprises three mechanically and electrically inter-connected compartments 101, 102, and 103. Compartments 101, 102, 103 are inter-connected by hinge mechanisms 104 (only one of which is shown in FIG. 2), thereby allowing TENS device 100 to conform to the curved anatomy of a user's leg. In a preferred embodiment, compartment 102 contains the TENS stimulation hardware (except for a battery) and user interface elements 106 and 108. In a preferred embodiment, compartments 101 and 103 are smaller, auxiliary compartments that house a battery for powering the TENS stimulation hardware and other ancillary elements, such as a wireless interface unit for allowing TENS device 100 to wirelessly communicate with other elements (e.g., a remote server). In another embodiment of the present invention, only one compartment 102 may be used for housing all of the TENS stimulation hardware, battery, and other ancillary elements without the need of side compartments 101 and 103.

Still looking at FIG. 2, interface element 106 comprises a push button for user control of electrical stimulation, and interface element 108 comprises an LED for indicating stimulation status and providing other feedback to the user. Additional user interface elements (e.g., an LCD display, audio feedback through a beeper or voice output, haptic devices such as a vibrating motor, etc.) are also contemplated and are considered to be within the scope of the present invention.

The preferred embodiment of the invention is designed to be worn on the user's upper calf 140 as shown in FIG. 1. TENS device 100, comprising stimulator 105, electrode array 120, and strap 110, is secured to upper calf 140 by placing the apparatus in position and then tightening strap 110. More particularly, electrode array 120 is deliberately sized and configured so that it will apply appropriate electrical stimulation to the appropriate anatomy of the user regardless of the specific rotational position of TENS device 100 on the leg of the user. Although the preferred embodiment comprises placement of the TENS device on the upper calf of the user, additional locations (such as above the knee, on the lower back, and on an upper extremity) are contemplated and are considered within the scope of the present invention.

Figure 3:
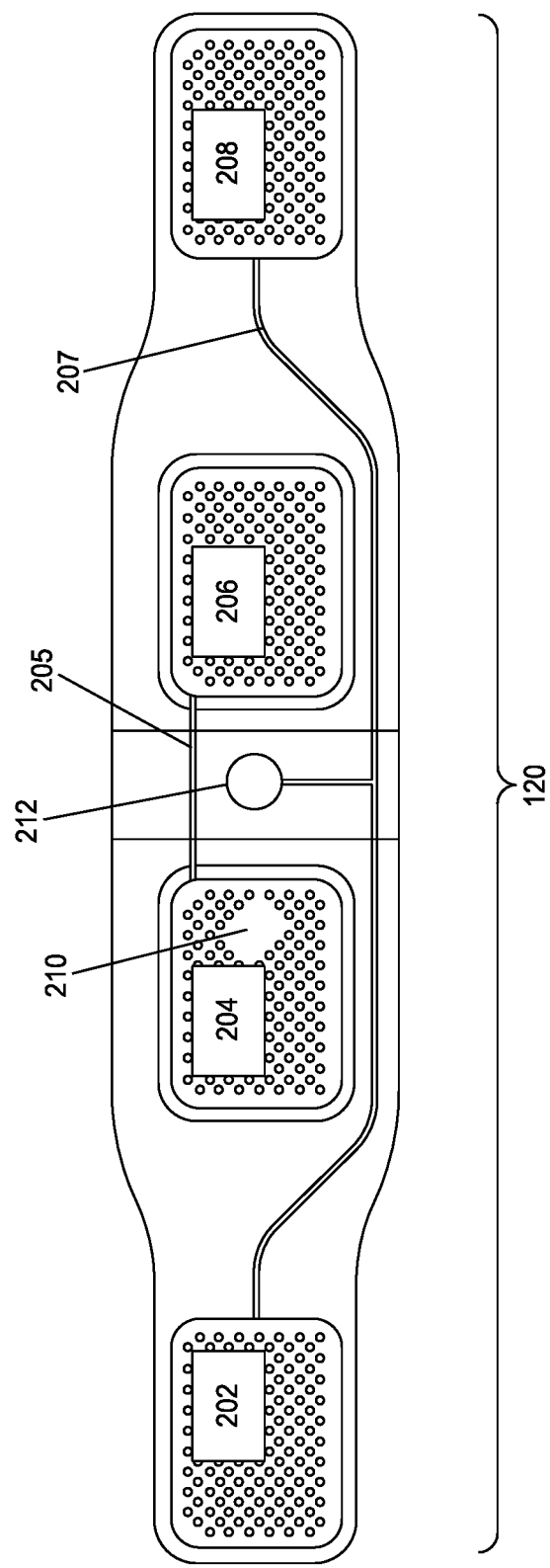
FIG. 3 is a schematic view showing the underside of the electrode array of the novel TENS device shown in FIGS. 1 and 2.

FIG. 3 shows a schematic view of one preferred embodiment of electrode array 120. Electrode array 120 preferably comprises four discrete electrodes 202, 204, 206, 208, each with an equal or similar size (e.g., surface area). Electrodes 202, 204, 206, 208 are preferably connected in pairs so that electrodes 204 and 206 (representing the cathode) are electrically connected to one another (e.g., via connector 205), and so that electrodes 202 and 208 (representing the anode) are electrically connected to one another (e.g., via connector 207). It should be appreciated that electrodes 202, 204, 206 and 208 are appropriately sized, and connected in pairs, so as to ensure adequate skin coverage regardless of the rotational position of electrode array 120 on the leg of a user. Furthermore, it should be appreciated that electrodes 202, 204, 206 and 208 are not connected in an interleaved fashion, but rather are connected so that the two inside electrodes 204 and 206 are connected to one another, and so that the two outside electrodes 202 and 208 are connected to one another. This electrode connection pattern ensures that if the two outer electrodes 202 and 208 should inadvertently come into contact with one another, an electrical short of the stimulation current flowing directly from cathode to anode will not occur. Electrical current (i.e., for electrical stimulation to the tissue) is provided to the electrode pairs 204, 206 and 202, 208 by connectors 210, 212 (see FIGS. 3 and 4) which mate with complementary connectors 130, 132 on stimulator 105. Connector 210 is electrically connected with electrodes 204 and 206, and connector 212 is electrically connected with electrodes 202 and 208. Stimulator 105 generates electrical currents that are passed through electrodes 204, 206 and electrodes 202, 208 via connectors 210, 212 respectively.

In a preferred embodiment, the skin-contacting conductive material is a hydrogel material which is built into electrodes 202, 204, 206, 208. The function of the hydrogel on the electrodes is to serve as an interface between the stimulator and the portion of the user's body in which the sensory nerves to be stimulated reside. Other types of electrodes such as dry electrodes and non-contact stimulation have also been contemplated and are considered within the scope of the present invention.

Further details regarding the construction and use of the foregoing aspects of TENS device 100 are disclosed in pending prior U.S. patent application Ser. No. 13/678,221, filed Nov. 15, 2012 by Shai N. Gozani et al. for APPARATUS AND METHOD FOR RELIEVING PAIN USING TRANSCUTANEOUS ELECTRICAL NERVE STIMULATION, which patent application is hereby incorporated herein by reference.

In a preferred embodiment, electrode array 120 will create an electrode-skin contact area of at least 28 cm² for each of the cathode and anode.

Unintended electrode peeling during a therapy session represents a potential hazard to the user due to increased current and power density which may cause user discomfort and, in the extreme, may pose a risk for thermal burns. The higher current and power density are caused by the same stimulation current flowing through a smaller contact area between the electrode and the user's skin as electrode peeling occurs.

Ideally, the electrode-skin contact area would be directly monitored during TENS stimulation and then the current and power density could be determined and stimulation terminated or reduced if a threshold for either current or power density was exceeded. However, from a practical perspective, the electrode-skin contact area cannot be easily measured in real-time.

In view of the foregoing, the present invention discloses a method to estimate electrode-skin contact area by monitoring changes in electrode-skin impedance. The method is based on the bioelectrical principle that the contact area is the dominant factor influencing changes in electrode-skin impedance during transcutaneous electrical stimulation [Lykken D T. Properties of electrodes used in electrodermal measurement. *J Comp Physiol Psychol.* October 1959; 52:629-634] [Lykken D T. Square-wave analysis of skin impedance. *Psychophysiology.* September 1970; 7(2):262-275].

Electrode-Skin Interface

Figure 5:
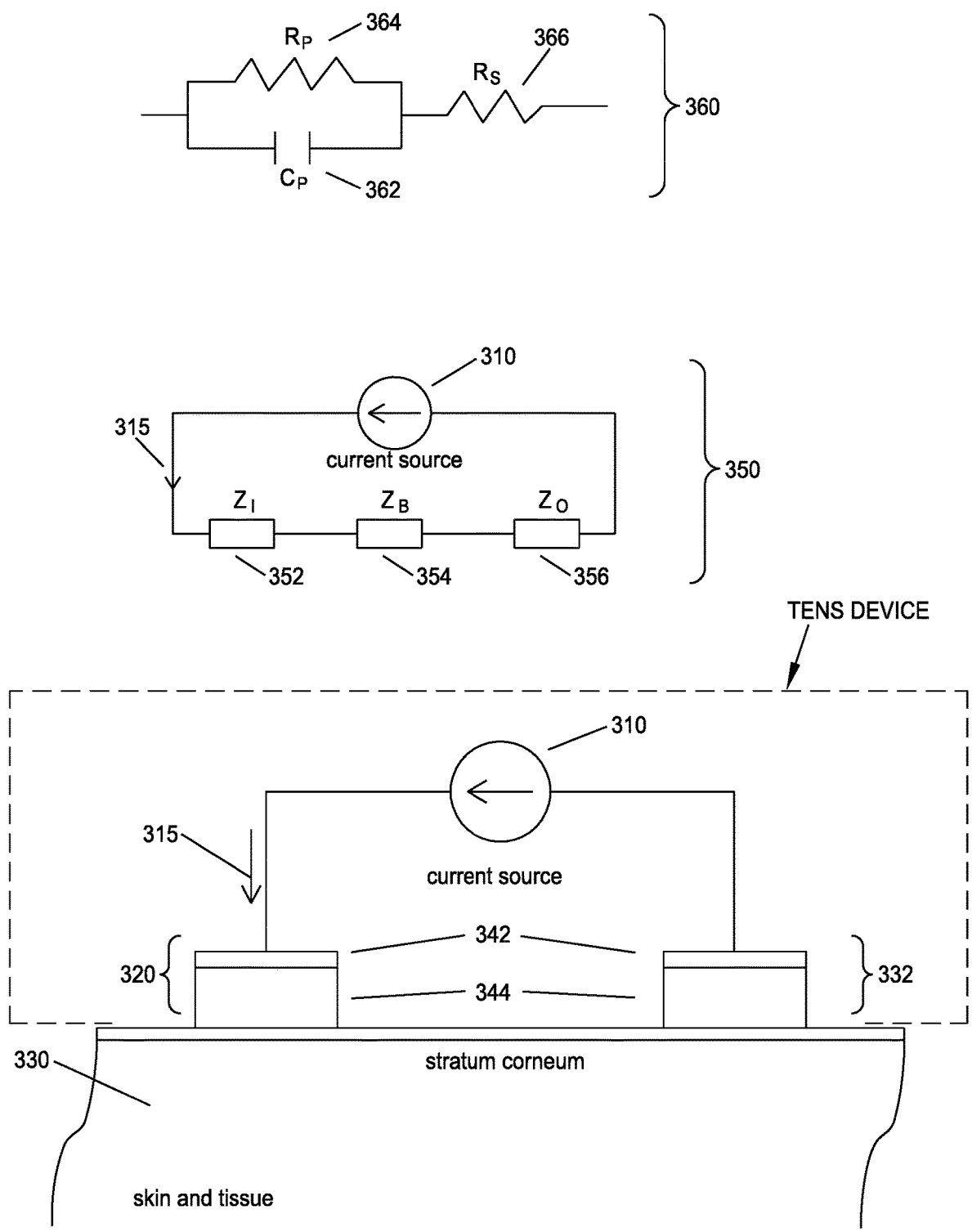
FIG. 5 is a schematic view of the electrode-skin interface of the novel TENS device shown in FIGS. 1 and 2, and its equivalent circuits for hydrogel electrodes placed against the skin.

The function of hydrogel electrodes is to serve as an interface between a transcutaneous electrical nerve stimulator (i.e., a TENS device) and the user's body in which the superficial sensory nerves to be stimulated reside. FIG. 5 is a schematic representation of the current flow between a TENS device and the user. FIG. 5 also shows an equivalent circuit representation 350 of the interface between the TENS device and the anatomy. As seen in FIG. 5, stimulation current 315 from a constant current source 310 flows into the user's skin 330 via cathode electrode 320. Cathode electrode 320 consists of conductive backing (e.g., silver hatch) 342 and hydrogel 344. The electrode-skin interface components 320 and 330 (i.e., cathode 320 and skin 330) provide an impedance to current flow that is included within the input impedance $Z_I$ 352 of the equivalent circuit 350. Once in the body, the current is subject to further impedance from various tissue components such as adipose tissue, muscle, nerve, and bone (not shown) that is represented by body impedance $Z_B$ 354 of the equivalent circuit 350. Finally, the current returns to current source 310 through another electrode-skin interface consisting of skin 330 and anode electrode 332 (anode electrode 332 also comprises a conductive backing 342 and hydrogel 344). The interface between skin 330 and anode electrode 332 is represented by output impedance $Z_O$ 356 in the equivalent circuit model 350. It should be appreciated that the designation of anode and cathode electrodes (and similarly input and output impedance) is purely notational. When the biphasic stimulation pulse reverses its polarity in its second phase of the TENS stimulation, current will be flowing into the user body via interface 332 and out of the body via interface 320.

The behavior of the electrode-skin interface $Z_I$ 352 and the electrode-skin interface $Z_O$ 356 of equivalent circuit 350 can be further modeled by the passive electrical circuit 360 [van Boxtel A. Skin resistance during square-wave electrical pulses of 1 to 10 mA. *Med Biol Eng Comput.* November 1977; 15(6):679-687]. The parallel capacitance $C_P$ 362 and resistance $R_P$ 364 of the passive electrical circuit 360 are associated with the stratum corneum. Component $R_S$ 366 of the passive electrical circuit 360 represents the aggregate series resistance and has components associated with several skin structures, including the stratum corneum.

The body impedance $Z_B$ 354 of equivalent circuit 350 depends on the type of tissue through which the stimulation current flows (e.g., adipose, muscle, nerve, bone, etc.). However, irrespective of the specific tissue path, $Z_B$ 354 of equivalent circuit 350 is typically much smaller than the electrode-skin impedances $Z_I$ 352 and $Z_O$ 356 of equivalent circuit 350. Because the three impedances in the equivalent circuit 350 are in series, the total impedance, Z, is the sum of individual impedances (Equation 1).

$$Z=Z_O+Z_B+Z_I \qquad \text{Eq. 1}$$

Equation 1 can be simplified by dropping the body impedance $Z_B$, since $Z_B \ll (Z_O - Z_I)$. Furthermore, since $Z_O$ and $Z_I$ have similar characteristics (e.g., hydrogel type, surface area, application to similar skin type, etc.), then the overall impedance, Z, can be simplified to Equation 2, where $Z_E$ is the common electrode-skin interface impedance.

$$Z=Z_O+Z_I=Z_E+Z_E=2Z_E \qquad \text{Eq. 2}$$

In the preferred embodiment, to simplify the model and align the impedances to practically measurable quantities, the electrode-skin impedance is defined using a pseudo resistance. Specifically, the pseudo resistance is given by the ratio of the voltage and current at the end of the stimulation pulse. In the case of a bi-phasic stimulation pulse, the voltage and current at the end of the first phase are used, although equivalent results are expected for the second phase. This square-wave analysis approach is commonly used to describe and study the behavior of the electrode-skin impedance. If the phase duration is long enough relative to the electrode-skin charging time constant, then the pseudo resistance approximates $R_P+R_S$ (of the passive electrical circuit 360 of FIG. 5).

Figure 6:
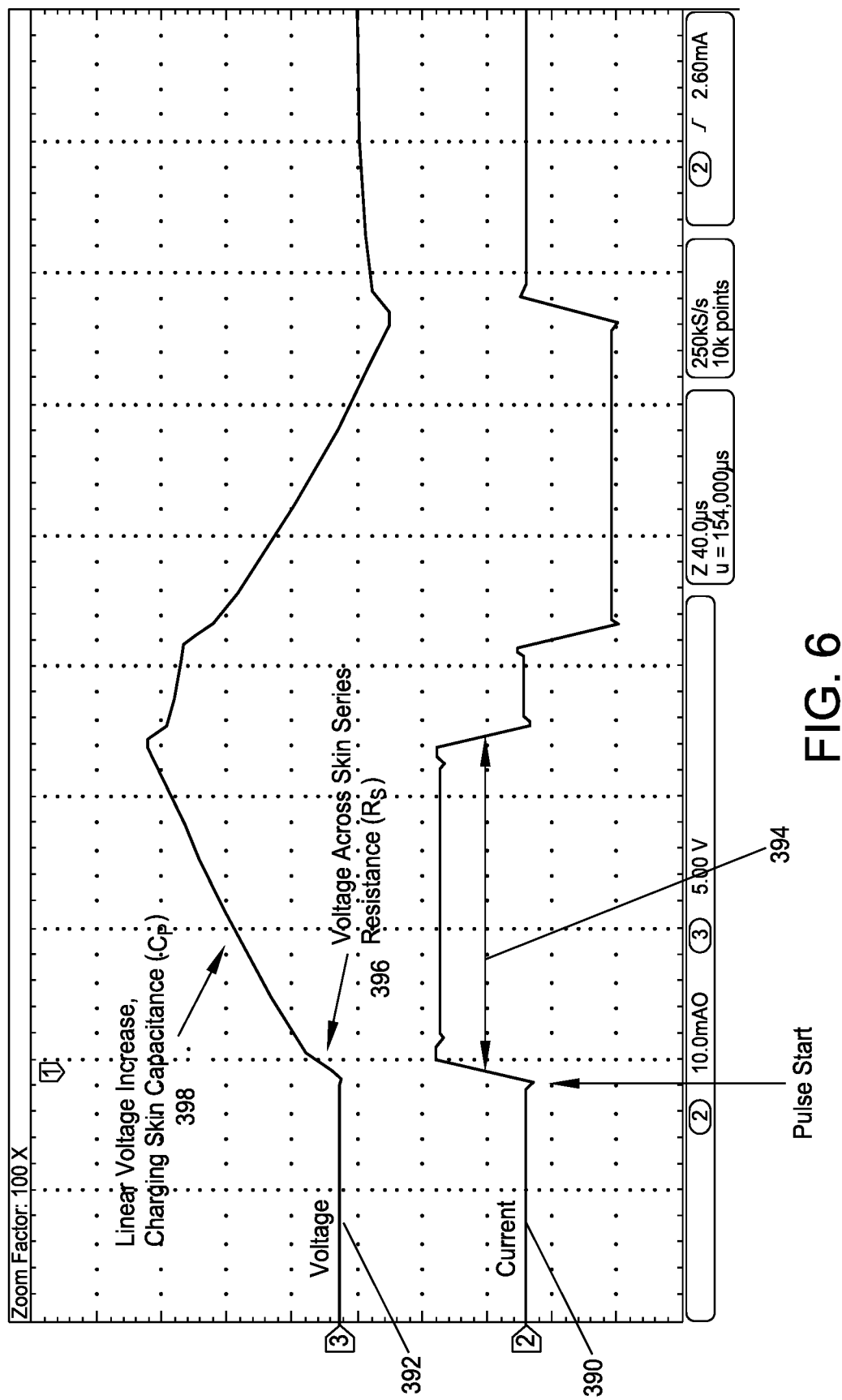
FIG. 6 is a screen capture of an oscilloscope trace showing that the current flow of the TENS device is mostly capacitive when the pulse duration is short.

FIG. 6 shows sample oscilloscope traces of current 390 through the impedance Z and the voltage 392 across the impedance Z. The pulse duration 394 is short in comparison to the electrode-skin charging time constant in this example, which is also true for most TENS stimulation situations. As a result, the pseudo resistance primarily represents charging (trace 398) of the capacitor $C_P$ 362 (of the passive electrical circuit 360 of FIG. 5) along with a small voltage drop 396 across the series resistance $R_S$ 366 (of the passive electrical circuit 360 of FIG. 5). Therefore, the pseudo resistance primarily represents the capacitive portion of the electrode-skin impedance Z.

"Electrode Peeling" Model

Several factors influence the electrode-skin impedance ($Z_E$), including contact area between the skin and electrode, physical and bioelectrical characteristics of the hydrogel, current density, and the skin condition [Lykken D T. Square-wave analysis of skin impedance. *Psychophysiology*. September 1970; 7(2):262-275] [van Boxtel A. Skin resistance during square-wave electrical pulses of 1 to 10 mA. *Med Biol Eng Comput*. November 1977; 15(6):679-687] [Keller T, Kuhn A. Electrodes for transcutaneous (surface) electrical stimulation. *J Automatic Control, University of Belgrade*. 2008; 18(2):35-45]. In the "electrode peeling" model developed here, the simplifying assumption is made that all the factors influencing the electrode-skin impedance, with the exception of contact area and current density, are stable during a TENS therapy session (a typical TENS therapy session lasts between 30 to 60 minutes). Although this assumption does not strictly hold, deviations from this idealized case are limited and can be accounted for by incorporating a safety factor when setting the detection threshold (i.e., when identifying the change in electrode-skin impedance which represents an unacceptable degree of "electrode peeling").

The electrode peeling model will be developed first with consideration only for contact area, and then the impact of current density will be addressed.

It is worth noting that the goal of this invention is to determine the relative changes in electrode-skin contact area as determined by changes in electrode-skin impedance. It is not the objective of this invention to estimate the precise contact area at any given moment.

The relationship between contact area and electrode-skin impedance can be modeled as an inverse linear one [Lykken D T. Square-wave analysis of skin impedance. *Psychophysi-ology*. September 1970; 7(2):262-275]. The relationship between the impedance, $Z_E$, and contact area, A, is expressed by Equation 3

$$Z_E = \frac{\rho}{A} \qquad \text{Eq. 3}$$

where ρ is a conversion constant from contact area to impedance that incorporates the effects of various factors that are assumed to be stable during a therapy session. If the contact area decreases such that the new contact area is αA, where 0<α≤1, then the impedance increases as shown in Equation 4.

$$Z_E = \frac{\rho}{\alpha A} \qquad \text{Eq. 4}$$

Although it is possible that both electrodes will peel (i.e., unintentionally detach from the skin of the user) and therefore their respective contact areas will decrease, it is more likely (and more conservative to assume) that only one electrode peels. Under this condition, the overall impedance (originally Equation 2) is given by Equation 5.

$$Z = \frac{\rho}{A} + \frac{\rho}{\alpha A} = \frac{\rho(1+\alpha)}{\alpha A} \qquad \text{Eq. 5}$$

The change in the overall impedance due to peeling of one electrode can be expressed as a ratio between the impedance at the start of the therapy session ($Z_{t=0}$) when the contact area is known to be the entire surface area A of the electrode, and the impedance ($Z_{t=T}$) at a later time, T, when the contact area has decreased to αA. The ratio is given in Equation 6.

$$\frac{Z_{t=T}}{Z_{t=0}} = \frac{(1+\alpha)}{2\alpha} \qquad \text{Eq. 6}$$

Thus far, only the impact of contact area on impedance has been accounted for.

Given a constant electrode-skin contact area, prior research suggests that the impedance will decrease with increased current density [Lykken D T. Square-wave analysis of skin impedance. *Psychophysiology*. September 1970; 7(2):262-275] [van Boxtel A. Skin resistance during square-wave electrical pulses of 1 to 10 mA. *Med Biol Eng Comput*. November 1977; 15(6):679-687] [Keller T, Kuhn A. Electrodes for transcutaneous (surface) electrical stimulation. *J Automatic Control, University of Belgrade*. 2008; 18(2):35-45]. Current density is defined as the current intensity per unit contact area. With a fixed overall current intensity, a decrease in electrode-skin contact area would increase the effective current density flowing through the remaining contact area, thus decreasing the impedance per unit area. In essence, as a result of decreased contact area, the impact of the escalating current density on impedance may partly offset the impact of decreasing contact area on the impedance. The effect of current density is modeled here as a multiplicative factor $\alpha^\delta$ with δ>0. Note that δ is inversely related to the current intensity (i.e., δ is largest for low stimulation current). The electrochemical properties of the conductive gel materials used in the electrodes may also impact the value of δ and can be determined experimentally or analytically. The complete "electrode peeling" model is shown in Equation 7 (note that the multiplicative factor is only applied to the peeling electrode).

$$\frac{Z_{t=T}}{Z_{t=0}} = \frac{1 + \alpha^{(\delta-1)}}{2} \qquad \text{Eq. 7}$$

Square-wave analyses of skin impedance have demonstrated that the aforementioned impact of current density on impedance is mediated (in the context of the passive electrical circuit 360 of FIG. 5) primarily through the parallel resistance, $R_P$, whereas $C_P$ and $R_S$ are mostly independent of current density [Lykken D T. Square-wave analysis of skin impedance. *Psychophysiology*. September 1970; 7(2):262-275] [van Boxtel A. Skin resistance during square-wave electrical pulses of 1 to 10 mA. *Med Biol Eng Comput*. November 1977; 15(6):679-687] [Kaczmarek K A, Webster J G, Bach-y-Rita P, Tompkins W J. Electrotactile and vibrotactile displays for sensory substitution systems. *IEEE Trans Biomed Eng*. January 1991; 38(1):1-16]. The impact of current density on electrode-skin impedance with a typical TENS device and electrode is therefore expected to be low. In a preferred embodiment of the novel TENS device 100, the stimulation pulse phase duration is 100 μsec, which is small relative to the electrode-skin impedance time constant (typically >1 millisecond). As a result, the impedance of the TENS stimulation is primarily capacitive rather than resistive, and thus the contribution of $R_P$ to the overall impedance, relative to $C_P$ and $R_S$, is small (see FIG. 6).

If δ<1, then current density partially or completely offsets the impact of decreasing contact area on impedance (see FIG. 6). At a low current intensity (e.g., below 10 mA), and long stimulation pulses (e.g., >1 millisecond) where $R_P$ is relevant, δ may be as high as 0.6-0.8 [van Boxtel A. Skin resistance during square-wave electrical pulses of 1 to 10 mA. *Med Biol Eng Comput*. November 1977; 15(6):679-687] [Keller T, Kuhn A. Electrodes for transcutaneous (surface) electrical stimulation. *J Automatic Control, University of Belgrade*. 2008; 18(2):35-45]. However, given the higher current intensity typically used with conventional TENS devices and the fact that the impedance of the TENS stimulation is mostly capacitive (i.e., current mostly flows through $C_P$ rather than $R_P$ when considered in the context of the passive electrical circuit 360 of FIG. 5), the expected value for δ is small. In support, experimental data obtained with at least one TENS device suggests that the impact of current density on impedance is small, and therefore for purposes of this model, δ is set to 0.1 in the following analysis.

Figure 7:
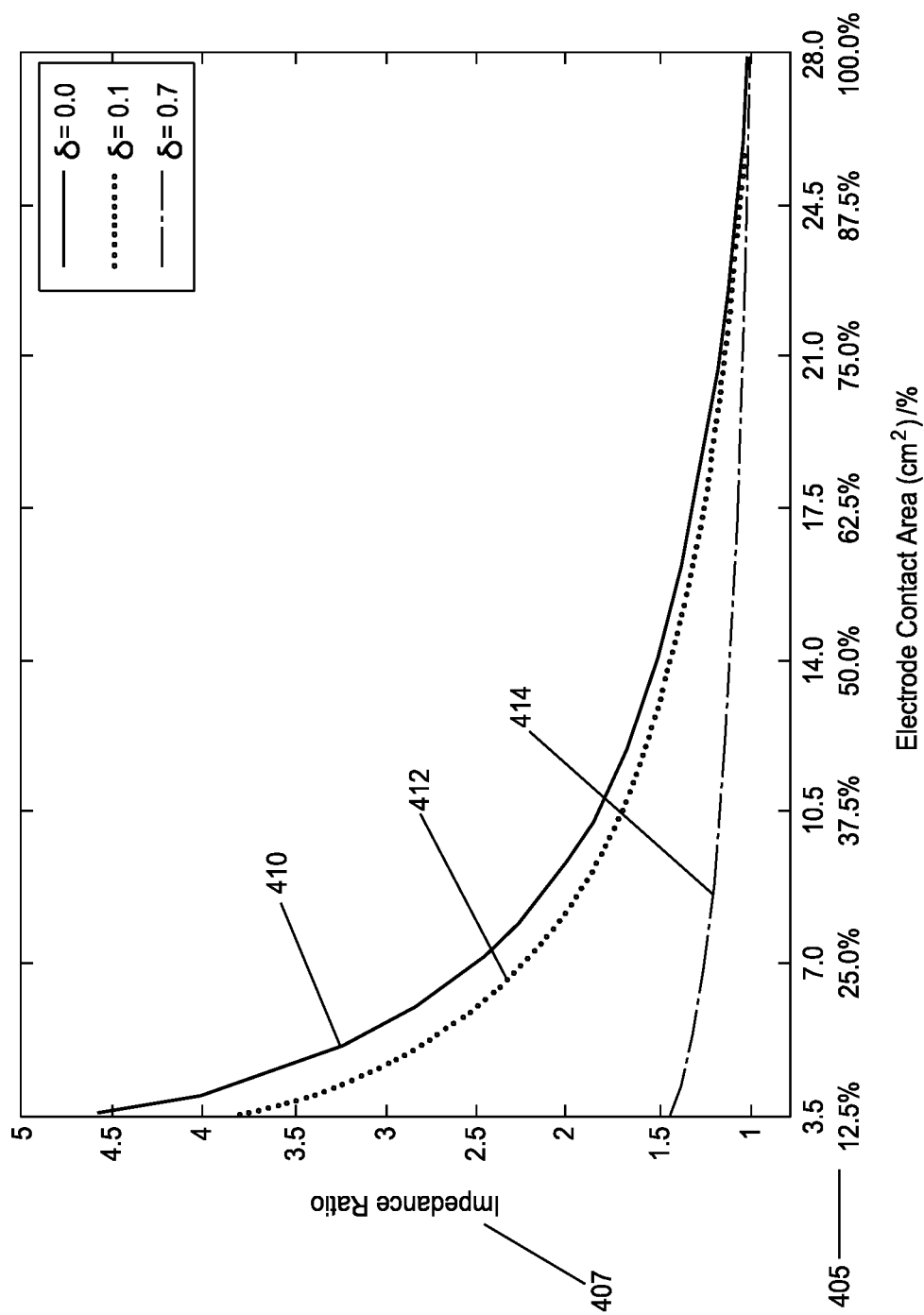
FIG. 7 is a schematic view showing the predicted relationship between contact area and impedance ratio for different δ values.

Three curves in FIG. 7 show the effects of the parameter value δ. curve 410 corresponds to δ=0.0, curve 412 corresponds to δ=0.1, and curve 414 corresponds to δ=0.7. X-axis 405 denotes the electrode-skin contact area in both absolute unit (cm²) and relative percentage of the initial area of 28 cm². Y-axis 407 is the impedance ratio between present impedance (i.e., $Z_{t=T}$) and baseline impedance (i.e., $Z_{t=0}$). As shown, the impedance ratio changes rapidly when the size of the contact area decreases to below 7 to 10 cm². This non-linearity in the area-impedance relationship provides a safety mechanism by making the electrode peeling detector highly sensitive to large reductions in electrode-skin contact area.

Because the electrode-skin impedance typically decreases with the duration of time the electrode is on the skin [van Boxtel A. Skin resistance during square-wave electrical pulses of 1 to 10 mA. *Med Biol Eng Comput*. November 1977; 15(6):679-687], which is not specifically modeled in Equation 7, we replace $Z_{t=0}$ with $Z_{t<T}$, where $Z_{t<T}$ is the minimum impedance for all time t<T. Thus, the final electrode peeling detector is given in Equation 8.

$$\text{If } \frac{Z_{t=T}}{Z_{t<T}} > \frac{1 + \alpha^{(\delta-1)}}{2} \text{ then halt stimulation} \qquad \text{Eq. 8}$$

In a preferred embodiment, TENS device 100 comprises an "electrode peeling" detector which comprises the circuitry and/or software for monitoring the electrode-skin impedance continuously during TENS stimulation by measuring the stimulation current 315 delivered by constant current stimulator 310 and by measuring the voltage difference between cathode 320 and anode 332 of the constant current stimulator 310. The total equivalent impedance "seen" by the stimulator 310 can be calculated by dividing the voltage difference by the current. The total impedance is dominated by the impedance $Z_I$ and $Z_O$ (of equivalent circuit 350) associated with the electrode-skin interface 320 and 332, which in turn is largely determined by the inverse of the contact area size. The initial total impedance is saved in memory and is referred to as the "baseline" impedance. The total impedance measured at each subsequent sample time T will update the baseline impedance $Z_{t<T}=\min(Z_{t<T-1}, Z_T)$. In other words, since the electrode-skin impedance typically decreases as a function of the length of time that the electrode is on the skin, the baseline impedance is preferably continuously updated so that it is set at the minimum impedance measured during the duration of that therapy session. The total impedance $Z_T$ is then compared against the baseline impedance value $Z_{t<T}$. If the electrode is peeling off the skin (i.e., if the electrode is unintentionally detaching from the skin), the electrode-skin contact area will decrease and the electrode-skin impedance will increase accordingly. The total impedance will also increase. Therefore, when the total impedance value exceeds a certain multiple of the baseline impedance value, one can infer that the electrode-skin contact area has fallen below a critical percentage of the full contact area. The transcutaneous electrical stimulation should then be stopped (or reduced) immediately in order to avoid excessive discomfort for the user and/or thermal burns due to high current and power density.

Figure 9:
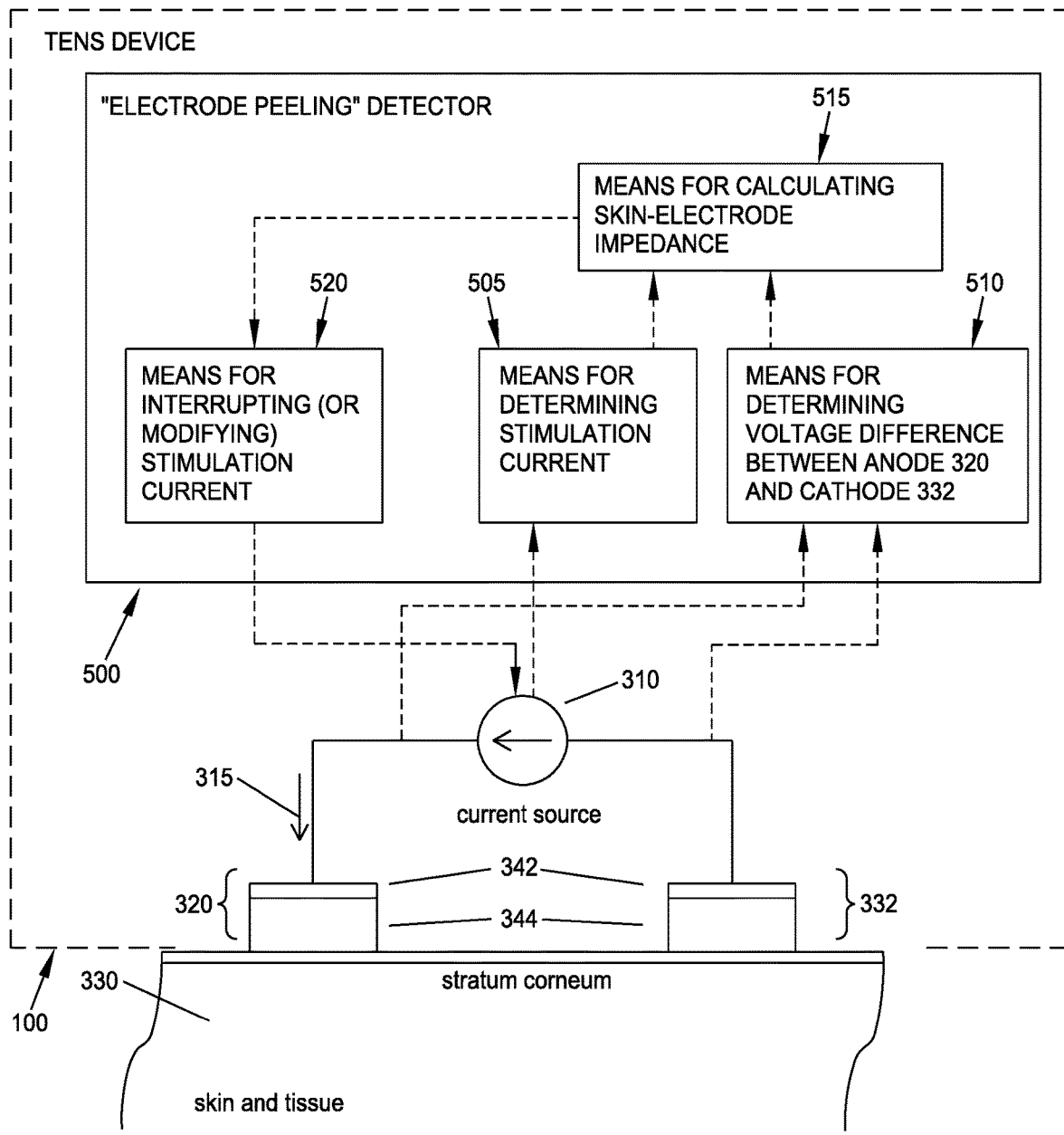
FIG. 9 is a schematic view showing the novel TENS device of FIGS. 1 and 2 and its "electrode peeling" detector.

See, for example, FIG. 9, which shows a TENS device 100 which comprises an "electrode peeling" detector 500, wherein electrode peeling detector 500 comprises means 505 for determining the stimulation current (e.g., a current sensor of the sort well known in the art), means 510 for determining the voltage difference between anode 320 and cathode 332 (e.g., a voltage sensor of the sort well known in the art), means 515 for calculating the electrode-skin impedance during transcutaneous electrical stimulation (e.g., a microprocessor of the sort well known in the art, with appropriate programming to provide the functionality disclosed herein), and means 520 for interrupting the stimulation current when the electrode-skin impedance exceeds a pre-determined threshold (e.g., a switch of the sort well known in the art, controlled by the aforementioned microprocessor so as to provide the functionality disclosed herein).

Figure 4:
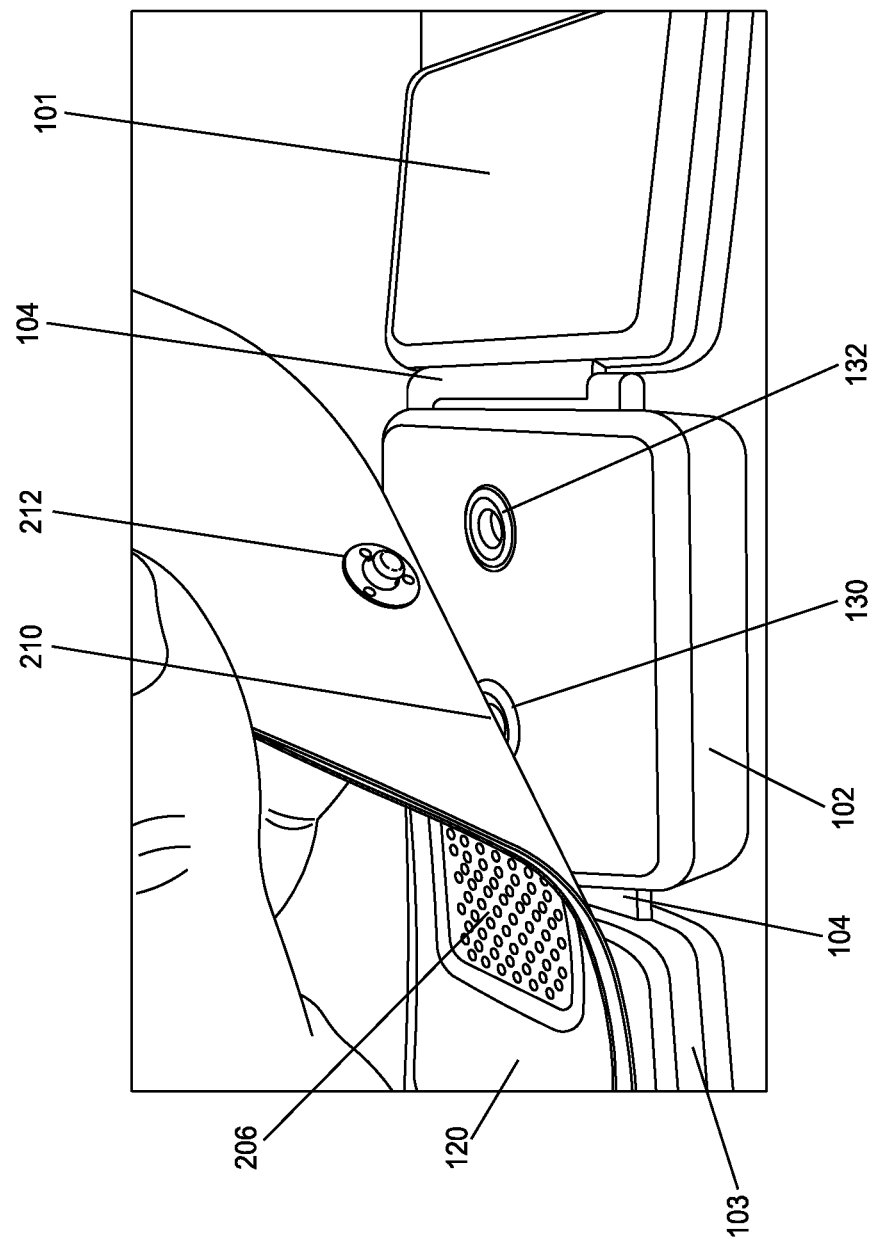
FIG. 4 is a schematic view showing the electrode array of FIG. 3 being electrically and mechanically connected to the stimulator of the novel TENS device shown in FIGS. 1 and 2.

The use of the preferred embodiment of the present invention is straightforward. The user snaps an electrode array 120 into stimulator 105 as shown in FIG. 4, thereby establishing a secure mechanical and electrical contact between the two components. Using strap 110, this assembly is then placed on the upper calf of the user with full electrode and skin contact (FIG. 1). Current stimulation for delivering TENS therapy is initiated by a pressing the push-button 106. The "electrode peeling" detector of the novel TENS device 100 will monitor the electrode-skin impedance throughout the therapy session by measuring voltage and current across anode and cathode terminals 210 and 212 of the stimulator 105. The baseline impedance is updated when a smaller impedance value is measured during the therapy session. When the ratio between the present electrode-skin impedance value and the baseline impedance value exceeds a pre-determined threshold, the "electrode peeling" detector of the TENS device will then cause the TENS device to stop stimulation. The LED 108 will blink red to indicate this condition, i.e., that the TENS device has stopped stimulation because the electrode-skin contact area has fallen below a critical value.

Application of the Electrode Peeling Model to TENS Therapy

The utility of the present invention was demonstrated in an experiment using a TENS device equipped with the "electrode peeling" detector as described below. The TENS device is designed to deliver stimulating current with intensity up to 100 mA. The biphasic stimulation pulse has a duration of 230 μsec (each phase is 100 μsec in duration, with 30 μsec gap between the two phases) and a random frequency of between 60 Hz and 100 Hz. The anode and cathode electrodes create an electrode-skin contact area of at least 28 cm$^2$ when the electrode array 120 is properly placed on the skin. Accordingly, the maximum average current density and power density are 0.5 mA/cm$^2$ and 3.6 mW/cm$^2$ respectively. Maximum average current density is the root mean square value of the biphasic current pulse with maximum intensity of 100 mA and maximum pulse frequency of 100 Hz. Power density is calculated under the same condition with a resistive load of 500Ω per FDA draft guidance [Food and Drug Administration, *Draft Guidance for Industry and Staff: Class II Special Controls Guidance Document: Transcutaneous Electrical Nerve Stimulator for Pain Relief*, Apr. 5, 2010]. The "electrode peeling" detector of the TENS device is designed to detect an electrode peeling event that results in a reduction of electrode-skin contact area by more than 87.5% (i.e., when the remaining electrode-skin contact area falls below one-eighth of the original electrode-skin contact area). When the electrode-skin contact area is at one-eighth of the original electrode-skin contact area size of 28 cm$^2$, the resulting maximum average power density is 28.5 mW/cm$^2$, still substantially below the 250 mW/cm$^2$ threshold identified as increasing the risk of thermal burns stated in the FDA draft guidance [Food and Drug Administration, *Draft Guidance for Industry and Staff: Class II Special Controls Guidance Document: Transcutaneous Electrical Nerve Stimulator for Pain Relief*, Apr. 5, 2010].

The impedance ratio between the impedance at present time and the baseline impedance is given by Equation 8. Experimental data obtained with the TENS device yield a value of 0.1 for parameter δ. To increase the safety margin and account for unrepresented factors and sources of variations, a 50% safety adjustment factor is incorporated in determining the impedance ratio threshold. Detecting a reduction of electrode-skin contact area by seven-eighths of the original size (α=0.125) leads to an impedance ratio threshold value of $0.5*[1.0+0.125^{(0.1-1.0)}]/2=1.87$. The final detection threshold value programmed into the "electrode peeling" detector of the TENS device was rounded down to 1.80. Thus, the "electrode peeling" detector of the TENS device will halt stimulation once it determines the present impedance is 180% or more of the baseline impedance.

A reduction in electrode-skin contact area is the primary cause for an impedance increase in TENS stimulation. In this experiment, reduction in electrode-skin contact area is accomplished through a controlled peeling process. The controlled peeling process is characterized by a pre-peel time and a peel rate. Pre-peel time refers to the duration of time that the electrode is on a subject's skin before electrode-skin contact area is reduced with controlled peeling. The peeling rate is the reduction of the electrode-skin contact area per minute. Peeling is accomplished by gradually lifting the electrode from the skin of the subject. For each study subject, one leg was randomly assigned to the 10 minute pre-peel time and the other to the 40 minute pre-peel time. The peel rate is randomly chosen between 1.5 and 60 cm$^2$/min for each test. This represents complete peeling of the outer electrodes 202 and 208 in approximately 30 seconds to 20 minutes.

Sixty-six subjects (37 females) participated in the experiment. The mean subject age was 51.3 with a standard deviation of 15.0 years and a range of 19 to 85 years (minimum to maximum). A different electrode was used in each leg. A total of 132 electrode peeling tests were conducted.

At the beginning of each test, an electrode 120 was placed on the selected leg of the subject and a TENS therapy session was initiated at an intensity of 5 mA. After the pre-peel time elapsed, one of the outer electrode pads 202 or 208 was peeled away from the skin at the designated peel rate. If necessary, the other outer pad was peeled away from the skin at the same peeling rate if the first pad was completely off the skin. The total outer electrode area remaining on the skin at the instant when stimulation automatically halted was logged.

Figure 8:
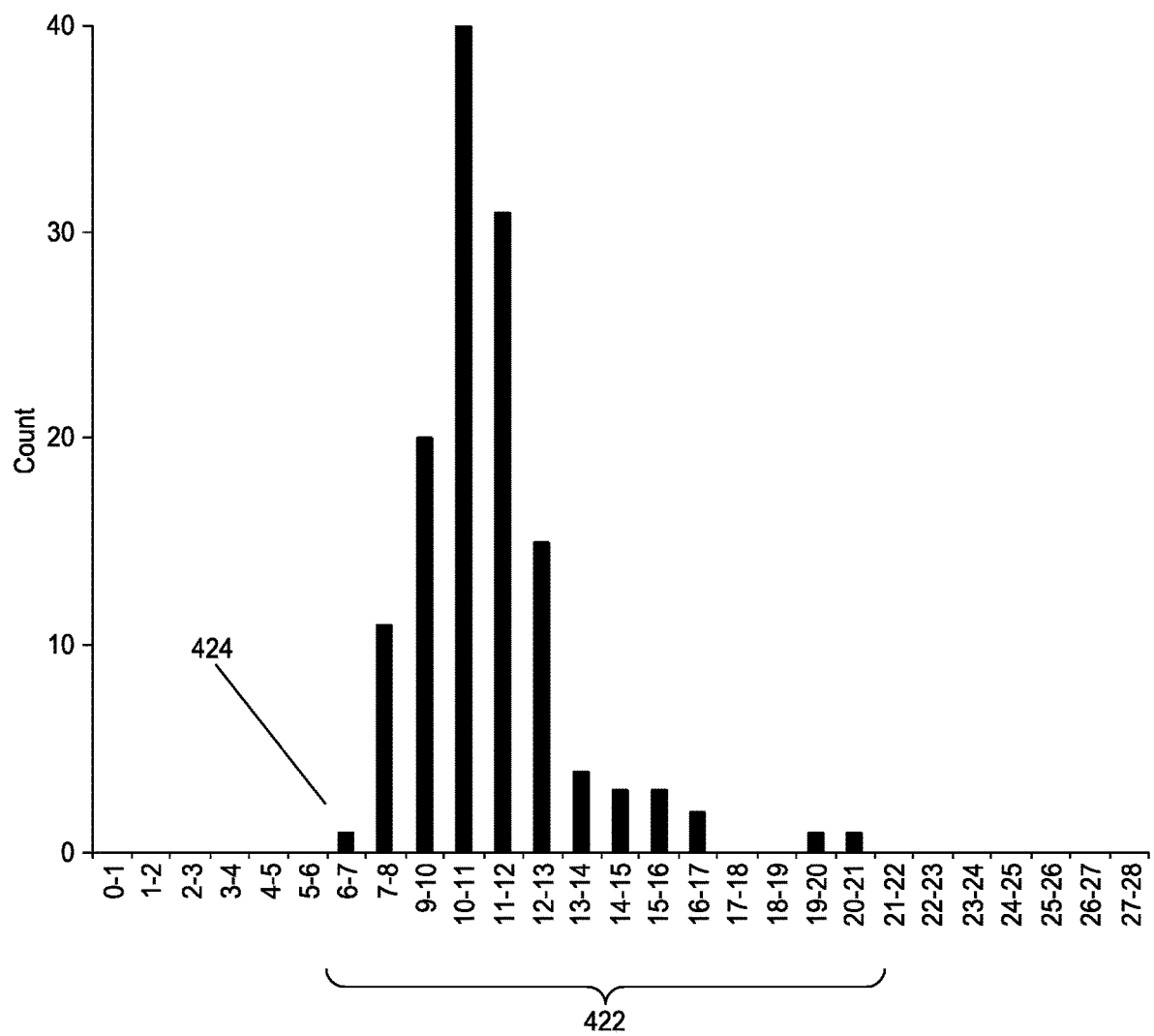
FIG. 8 is a schematic view showing, for a variety of electrode peeling tests, the distribution of electrode contact area ($cm^2$) remaining at the point at which an "electrode peeling" condition occurs, i.e., when the impedance ratio (present impedance divided by baseline impedance, updated if appropriate) exceeds a threshold value.

The distribution of remaining electrode contact areas 422 (in cm$^2$) triggering the electrode peeling condition is shown in FIG. 8. In other words, FIG. 8 shows a distribution, for the 132 electrode peeling tests conducted, of the electrode contact area (in cm$^2$) remaining at the point at which the electrode peeling condition occurs, i.e., the impedance ratio (present impedance divided by baseline impedance, updated if appropriate) exceeds the threshold value of 1.80. The minimum remaining electrode-skin contact area 424 was 6.9 cm$^2$, about twice as large as the target minimum contact area of 3.5 cm$^2$. Stimulation was halted by the TENS device for all 132 tests before the electrode-skin contact area fell below the minimum contact area of 3.5 cm$^2$. The average electrode-skin contact area at the time when electrode peeling was detected was 10.2±2.1 cm$^2$ and 10.1±1.7 cm$^2$, respectively for the 10 and 40 min pre-peeling time groups. The difference between the mean electrode-skin contact area for the two groups was not statistically significant (p>0.05, paired t-test). The average contact area was 10.1±1.9 cm$^2$ when all 132 tests were combined. The relationships between the remaining contact area and demographic factors, as well as between the remaining contact area and electrode peeling rate, were evaluated by univariate linear regression in the case of continuous variables (peel-rate, age, height, weight, and body mass index) and two-group t-test for categorical variables (gender). Neither peel-rate nor any demographic variable was predictive of remaining contact area (all p>0.05).

The experimental results demonstrated that electrode peeling can be reliably detected via real-time monitoring of the electrode-skin impedance. The fact that the contact area has no statistically significant correlation with test subject demographics and pre-peel time suggests that the detection of electrode peeling based on impedance monitoring is robust. As such, the "electrode peeling" detector should operate consistently in the face of variations in user and electrode characteristics.

Modifications of the Preferred Embodiments

In another embodiment of the present invention, the baseline impedance is the initial impedance value, instead of being the running minimum impedance value of all impedance values acquired up to that time instance.

In another embodiment of the present invention, instead of halting stimulation when the impedance ratio exceeds a pre-determined threshold, the TENS stimulation current intensity may be decreased proportionally to the estimated reduction in electrode-skin contact area. This approach will allow therapy to continue while maintaining the current and power density at a level below the safety threshold.

Each therapy session normally lasts about one hour. In one preferred embodiment, each therapy session is initiated when the user actuates the push button 106. In another preferred embodiment, a timer is used to initiate subsequent therapy sessions without further user intervention. This approach is especially useful when more than one therapy session is desired during sleep at night. When the first therapy session manually initiated by the user is completed, a timer starts automatically with a pre-set time period and the baseline impedance is saved for subsequent therapy sessions. In one embodiment, the timer period is the same as the duration of the prior therapy session. Expiration of the timer starts a new therapy session and the final baseline impedance from the prior session is used as the initial value of the baseline impedance for the present therapy session.

In a preferred embodiment of the present invention, the stimulation current intensity may increase or decrease as a therapy session progresses. For example, an increase may be necessitated by nerve habituation compensation. Therefore, the stimulation current intensity used to estimate the total impedance may be different within a therapy session or across multiple sessions.

In another embodiment, the total impedance is assessed by a dedicated probing current with fixed characteristics (e.g., stimulation current intensity and pulse duration). The intensity can be set to a level below the electrotactile sensation threshold intensity so that the probing current will not interfere with therapeutic electrical stimulation. The probing current pulse can have a duration much longer than therapeutic current pulse so that both resistive and capacitive components of the impedance can be evaluated.

In another embodiment of the invention, electrode-skin contact area is monitored during both TENS therapy sessions and the period between therapy sessions. The same probing current with stimulation intensity below the sensation threshold intensity is used during the off period to monitor the electrode-skin impedance.

Finally, it should be understood that additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for transcutaneous electrical nerve stimulation in a user, the apparatus comprising:
a stimulation unit for electrically stimulating at least one nerve;
an electrode array connectable to said stimulation unit, said electrode array comprising a plurality of electrodes for electrical stimulation of the at least one nerve;
a monitoring unit electrically connected to said stimulation unit for monitoring the impedance of the electrical stimulation through said electrode array; and
an analysis unit for analyzing said impedance to estimate a change of the impedance over time;
wherein said stimulation unit automatically alters the electrical stimulation of said stimulation unit when said analysis unit determines that the monitored electrode-skin impedance value has changed significantly; and
further wherein the change in the impedance value at a given time is quantified by an impedance ratio between the impedance value at that time and a baseline impedance value.

2. Apparatus according to claim 1 wherein said monitoring of the impedance is accomplished with the same electrical stimulation as that used to stimulate said at least one nerve.

3. Apparatus according to claim 1 wherein said monitoring of the impedance is accomplished with different electrical stimulation than that used to stimulate said at least one nerve.

4. Apparatus according to claim 3 wherein the electrical stimulation used for monitoring of the impedance has an intensity that is below the electrotactile sensation threshold of the user.

5. Apparatus according to claim 1 wherein a history of the electrode-skin impedance values is stored by said monitoring unit.

6. Apparatus according to claim 5 wherein the baseline impedance value is the first available impedance value from the impedance history.

7. Apparatus according to claim 1 wherein the baseline impedance value is the minimum among all available impedance values.

8. Apparatus according to claim 1 wherein said significant change is defined as that where the impedance ratio exceeds an impedance ratio threshold.

9. Apparatus according to claim 1 wherein the alteration to the electrical stimulation is to terminate stimulation.

10. Apparatus according to claim 1 wherein the alteration to the electrical stimulation is to inversely scale the electrical stimulation intensity by the impedance ratio.

11. Apparatus according to claim 1 wherein the monitoring unit monitors the impedance during stimulation.

12. Apparatus according to claim 1 wherein the monitoring unit monitors the impedance after the stimulation unit electrically stimulates the at least one nerve.

13. A method for delivering transcutaneous electrical nerve stimulation to at least one nerve of a user through an electrode array comprising a plurality of electrodes, the method comprising the steps of:
applying the electrode array to the surface of the user's skin;
electrically stimulating said at least one nerve of the user with an electrical stimulator connected to the electrode array;
monitoring the impedance of the electrode-skin interface;
analyzing the monitored impedance at at least two different time instances in order to determine a change in said impedance; and automatically altering the electrical stimulation based on changes in the monitored impedance of the electrode-skin interface.

14. A method according to claim 13 wherein monitoring of the impedance is accomplished with different electrical stimulation than that used to stimulate the at least one nerve.

15. A method according to claim 14 wherein the electrical stimulation used for monitoring of the impedance has an intensity that is below the electrotactile sensation threshold of the user.

16. A method according to claim 14 wherein the electrical stimulation used for monitoring of the impedance is continuously active regardless of the status of the electrical stimulation used to stimulate the at least one nerve.

17. A method according to claim 13 wherein the impedance is monitored by dividing the anode-cathode voltage difference by the stimulation current of the electrical stimulation used for monitoring at a particular time in the electrical stimulation.

18. A method according to claim 13 wherein the impedance is monitored by fitting the anode-cathode voltage difference curve using a parametric model of electrode-skin interface impedance.

19. A method according to claim 13 wherein change in the impedance is quantified by an impedance ratio between a currently monitored impedance value and a baseline impedance value.

20. A method according to claim 19 wherein the baseline impedance value is the first available impedance value from the impedance history.

21. A method according to claim 19 wherein the baseline impedance value is a percentile of all available impedance values from the impedance history.

22. Apparatus for transcutaneous electrical nerve stimulation in a user, the apparatus comprising:
a stimulation unit for electrically stimulating at least one nerve;
an electrode array connectable to said stimulation unit, said electrode array comprising a plurality of electrodes for electrical stimulation of the at least one nerve;
a monitoring unit electrically connected to said stimulation unit for monitoring the impedance of the electrical stimulation through said electrode array; and
an analysis unit for analyzing said impedance to estimate a change of the impedance over time;
wherein said stimulation unit alters the electrical stimulation of said stimulation unit when said analysis unit determines that the monitored electrode-skin impedance value has changed significantly, wherein the alteration to the electrical stimulation is to inversely scale the electrical stimulation intensity by the impedance ratio; and
further wherein the change in the impedance value at a given time is quantified by an impedance ratio between the impedance value at that time and a baseline impedance value.

23. A method for delivering transcutaneous electrical nerve stimulation to at least one nerve of a user through an electrode array comprising a plurality of electrodes, the method comprising the steps of:
applying the electrode array to the surface of the user's skin;
electrically stimulating said at least one nerve of the user with an electrical stimulator connected to the electrode array;
monitoring the impedance of the electrode-skin interface;
analyzing the monitored impedance at at least two different time instances in order to determine a change in said impedance; and
altering the electrical stimulation based on changes in the monitored impedance of the electrode-skin interface;
wherein the impedance is monitored by dividing the anode-cathode voltage difference by the stimulation current of the electrical stimulation used for monitoring at a particular time in the electrical stimulation.

24. A method for delivering transcutaneous electrical nerve stimulation to at least one nerve of a user through an electrode array comprising a plurality of electrodes, the method comprising the steps of:
applying the electrode array to the surface of the user's skin;
electrically stimulating said at least one nerve of the user with an electrical stimulator connected to the electrode array;
monitoring the impedance of the electrode-skin interface;
analyzing the monitored impedance at at least two different time instances in order to determine a change in said impedance; and
altering the electrical stimulation based on changes in the monitored impedance of the electrode-skin interface;
wherein the impedance is monitored by fitting the anode-cathode voltage difference curve using a parametric model of electrode-skin interface impedance.

\* \* \* \* \*